(12) United States Patent
McAfee

(10) Patent No.: US 10,299,937 B2
(45) Date of Patent: May 28, 2019

(54) EXPANDABLE SPINAL IMPLANT AND FLEXIBLE DRIVER

(71) Applicant: GLOBUS MEDICAL, INC., Audubon, PA (US)

(72) Inventor: Paul C. McAfee, Sparks, MD (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 15/375,842

(22) Filed: Dec. 12, 2016

(65) Prior Publication Data

US 2017/0086986 A1   Mar. 30, 2017

Related U.S. Application Data

(63) Continuation of application No. 13/525,944, filed on Jun. 18, 2012, now Pat. No. 9,549,824.

(60) Provisional application No. 61/499,855, filed on Jun. 22, 2011, provisional application No. 61/498,279, filed on Jun. 17, 2011.

(51) Int. Cl.
*A61F 2/44* (2006.01)
*A61F 2/46* (2006.01)
*A61F 2/30* (2006.01)
*A61F 2/28* (2006.01)

(52) U.S. Cl.
CPC ............. *A61F 2/447* (2013.01); *A61F 2/442* (2013.01); *A61F 2/4611* (2013.01); *A61F 2/30771* (2013.01); *A61F 2002/2835* (2013.01); *A61F 2002/3008* (2013.01); *A61F 2002/30014* (2013.01); *A61F 2002/3037* (2013.01); *A61F 2002/30405* (2013.01); *A61F 2002/30408* (2013.01); *A61F 2002/30411* (2013.01); *A61F 2002/30413* (2013.01); *A61F 2002/30418* (2013.01); *A61F 2002/30509* (2013.01); *A61F 2002/30512* (2013.01); *A61F 2002/30515* (2013.01); *A61F 2002/30556* (2013.01); *A61F 2002/30566* (2013.01); *A61F 2002/30579* (2013.01); *A61F 2002/30785* (2013.01); *A61F 2002/4475* (2013.01); *A61F 2002/4622* (2013.01); *A61F 2002/4629* (2013.01); *A61F 2002/4638* (2013.01); *A61F 2310/00017* (2013.01); *A61F 2310/00023* (2013.01)

(58) Field of Classification Search
CPC .................. A61F 2/4455; A61F 2/4611; A61F 2002/4495; A61F 2002/30133
USPC ...................................................... 606/96, 104
See application file for complete search history.

(56) References Cited

U.S. PATENT DOCUMENTS

| 4,863,476 A | * | 9/1989 | Shepperd | ............... | A61F 2/4455 623/17.15 |
| 2006/0129147 A1 | * | 6/2006 | Biedermann | ...... | A61B 17/7004 128/897 |

(Continued)

*Primary Examiner* — Matthew J Lawson

(57) ABSTRACT

Expandable spinal implants and drivers connected by a bendable joint are disclosed. The flexible connector allows the implant and driver to move to different angular orientations with respect to each other, and to apply rotational force or torque from the driver to the implant and its expansion mechanism. During insertion of an implant into the desired position, the driver may be oriented in the same or different direction than the long axis of the implant. After the spinal implant is placed in the desired position, the driver is used to expand the implant in selected dimensions.

17 Claims, 7 Drawing Sheets

(56) References Cited

U.S. PATENT DOCUMENTS

| | | | |
|---|---|---|---|
| 2008/0147193 A1* | 6/2008 | Matthis | A61F 2/4425 623/17.16 |
| 2008/0215061 A1* | 9/2008 | Schumacher | B25B 23/108 606/104 |
| 2009/0088852 A1* | 4/2009 | Chee | A61F 2/442 623/17.16 |
| 2009/0270873 A1* | 10/2009 | Fabian | A61F 2/442 606/99 |
| 2010/0268338 A1* | 10/2010 | Melkent | A61F 2/44 623/17.11 |
| 2011/0015747 A1* | 1/2011 | McManus | A61F 2/44 623/17.16 |

* cited by examiner

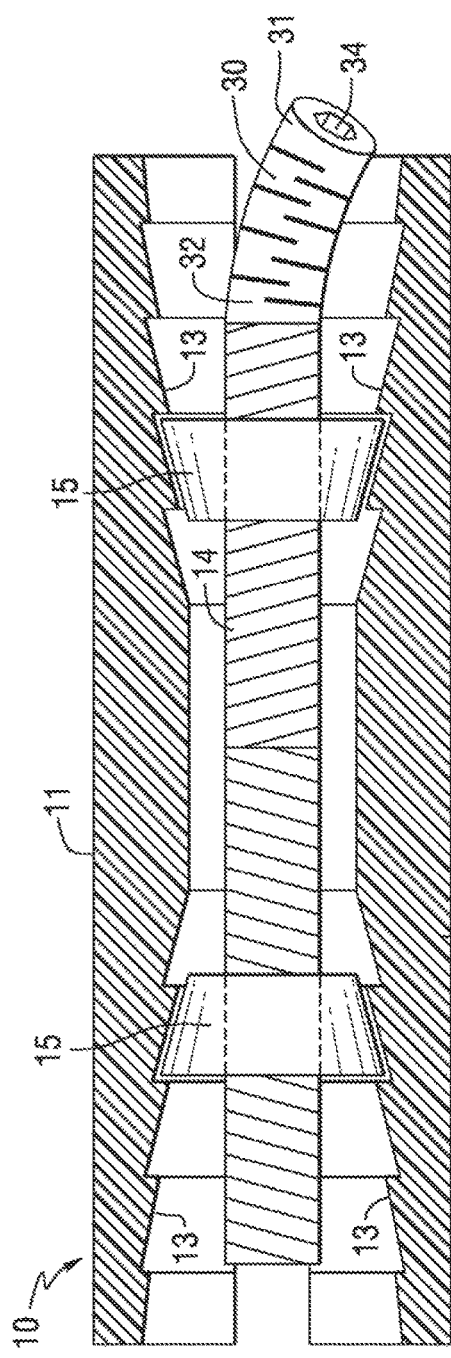
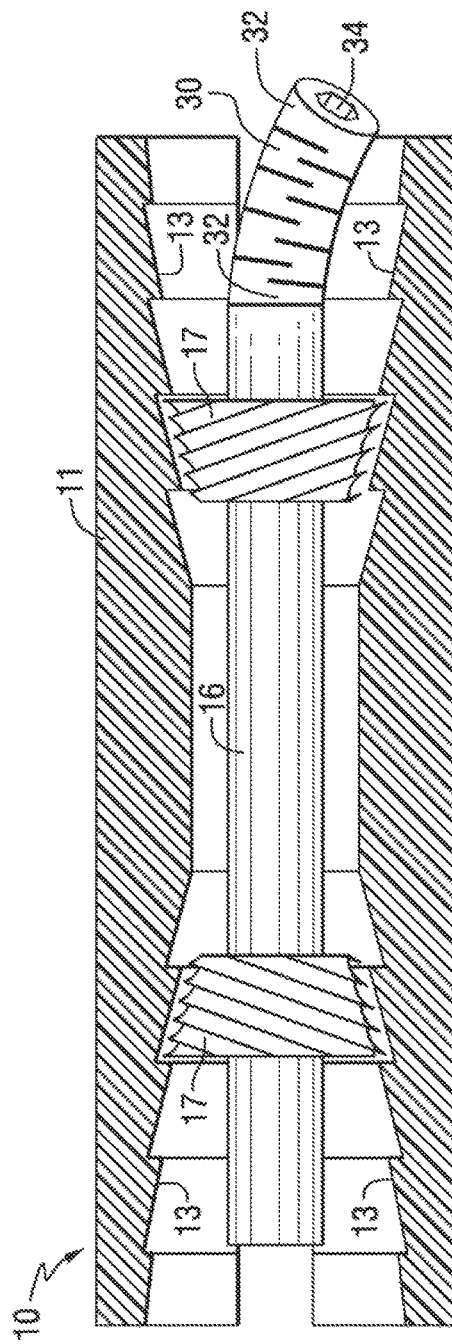
FIG. 9
FIG. 10 ent parallel or oblique, or in kyphosis or lordosis, compared to the original configuration of the implant.

EXPANDABLE SPINAL IMPLANT AND FLEXIBLE DRIVER

CROSS-REFERENCE TO RELATED APPLICATIONS

This application is a continuation of U.S. patent application Ser. No. 13/525,944, filed on Jun. 18, 2012 which claims the benefit of U.S. Provisional Patent Application Ser. No. 61/498,279 filed Jun. 17, 2011 and U.S. Provisional Patent Application Ser. No. 61/499,855 filed Jun. 22, 2011, all of which are incorporated herein by reference.

FIELD OF THE INVENTION

The present invention relates to spinal surgery, such as spinal fixation, and more particularly relates to expandable spinal implants and flexible drivers for positioning and expanding the implants.

BACKGROUND INFORMATION

Spinal implant surgery may be performed by a posterior lumbar interbody fusion (PLIF) approach, a transforaminal lumbar interbody fusion (TLIF) approach, or an extreme lateral interbody fusion (XLIF) approach. In these procedures, implants are inserted in desired positions in relation to the spine. Current spinal implant designs require an end approach deployment mechanism that is not satisfactory for certain procedures. For example, with scoliosis in the thoracolumbar spine, an orthogonal approach is often not possible. Additionally, with TLIF approaches utilizing expandable implants, the deployment has to be performed after the implant, e.g., cage or intervertebral spacer, has been turned inside the disk space. This prevents access to adjust the height of the implant after the implant has been turned, and makes extraction or removal problematic.

Current expandable implant designs are limited to PLIF type of approaches because the implants cannot be turned or collapsed. However, with PLIF approaches, there may be a risk that the expanded implant or cage extrudes back into the nerves of the spinal canal along the direction of its original insertion. In contrast, when a spacer is inserted with a TLIF approach, it is turned such that the trajectory is along the wide axis (side-to-side) of the vertebral body and the implant cannot migrate out backwards into the spinal canal.

SUMMARY OF THE INVENTION

The present invention provides expandable spinal implants and flexible drivers connected by a bendable joint that allow surgeons more flexibility when performing spinal surgeries. The connection between the driver and the implant includes a bendable joint, such as a helical high torque spring, that allows the implant and driver to move to different angular orientations with respect to each other, and to apply rotational force or torque from the driver to the implant and its expansion mechanism. During insertion of an implant into the desired position, the driver may be oriented in a direction different than the long axis of the implant. After the spinal implant is placed in the desired position, the driver is used to expand the implant in selected dimensions. In certain embodiments, the implants may include separate endplates which are connected by a mechanical connection which allows expansion or contraction. The endplates may be adjusted by the driver in parallel or oblique, or in kyphosis or lordosis, compared to the original configuration of the implant.

An aspect of the present invention is to provide a surgical instrument comprising a driver, an expandable spinal implant, and a flexible connector connected to the driver and the implant, wherein the flexible connector is rotatable by the driver to expand the spinal implant.

Another aspect of the present invention is to provide a surgical instrument comprising a driver having a proximal end and a distal end, and a flexible connector releasably attached to the distal end of the driver, wherein the flexible connector is structured and arranged to engage and expand a spinal implant when torque is applied to the flexible connector from the driver.

A further aspect of the present invention is to provide an expandable spinal implant comprising upper and lower plates expandable away from each other, an expansion mechanism structured and arranged to move the upper and lower plates away from each other, and a flexible connector engageable with the expansion mechanism.

Another aspect of the present invention is to provide a method of positioning and expanding a spinal implant in a patient. The method comprises grasping the implant with a driver in an aligned insertion orientation, positioning the implant in the patient at a desired position while rotating the implant from the aligned insertion orientation to an angled orientation, expanding the implant with the driver while the implant is in the angled orientation, and disengaging the driver from the implant.

These and other aspects of the present invention will be more apparent from the following description.

BRIEF DESCRIPTION OF THE DRAWINGS

FIG. 9 is a partially schematic side view of an expandable implant and flexible connector in accordance with an embodiment of the invention.

FIG. 10 is a partially schematic side view of an expandable implant and flexible connector in accordance with another embodiment of the invention.

DETAILED DESCRIPTION

The present invention provides apparatus and methods for surgical procedures in which an expandable implant is positioned and deployed in a patient by means of a driver and a flexible connector. The driver may be used to both position the implant in the desired location in relation to spinal vertebrae, and to expand the implant after it is positioned. The flexible connector transfers torque from the driver to thereby expand the implant, and is detachable from the driver or implant after the implant is expanded.

Figure 1:
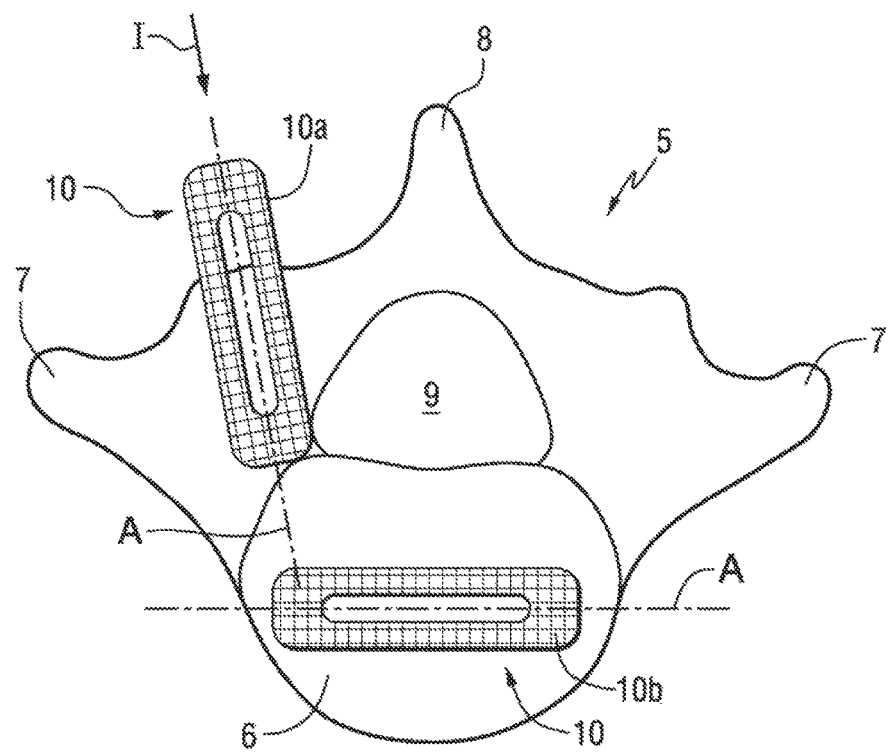
FIG. 1 illustrates a TLIF spinal procedure in which an implant is initially inserted in one orientation, and then rotated into the desired position in relation to the spinal vertebrae.

FIG. 1 schematically illustrates a TLIF spinal procedure in which an expandable implant is initially inserted in one orientation, and then rotated into the desired position in relation to the spinal vertebrae. As shown in FIG. 1, a spinal vertebra 5 comprising a vertebral body 6, transverse process 7, spinous process 8 and spinal canal 9 is subject to a TLIF implant procedure. An implant generally labeled as element 10 is initially inserted between the transverse process 7 and spinous process 8, while substantially avoiding the spinal canal 9. During an initial insertion stage, the implant 10a is oriented as shown with its longitudinal or axial direction A corresponding to the initial direction of insertion I. Subsequently, the implant is moved to its final desired position, labeled as 10b, in which the axial direction A of the implant 10b is aligned in a direction substantially transverse to the spinal vertebra 5. The bottom face of the implant 10b may contact the anterior one-third of the vertebral body 6, while the top face of the implant 10b contacts the vertebral end plates of an adjacent vertebra in the spine (not shown). As described above, the TLIF procedure illustrated in FIG. 1 advantageously orients the implant 10b along a longer dimension of the vertebral body 6, and in a direction that does not intersect the spinal canal 9.

Figure 2:
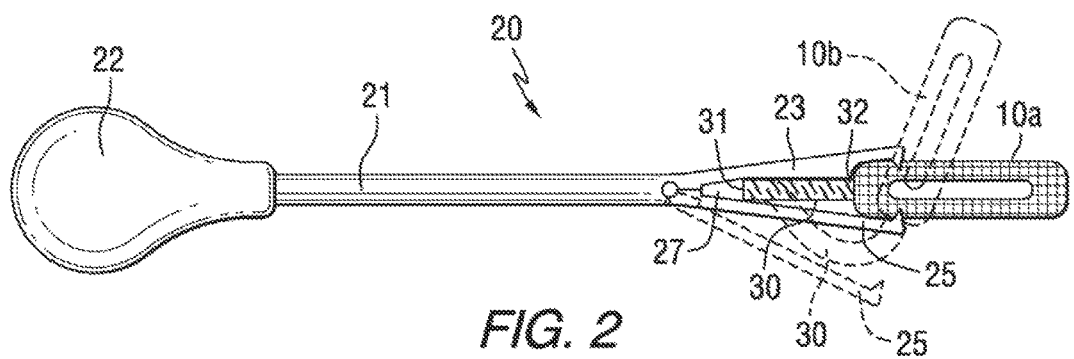
FIG. 2 is a partially schematic top view of an implant, driver and flexible connector, showing the arrangement of the components during an initial insertion stage, and also showing the arrangement of the components during a subsequent expansion stage (in phantom), in accordance with an embodiment of the invention.

FIG. 2 is a partially schematic illustration showing the initial arrangement of an implant 10a, driver 20 and flexible connector 30 during an implant procedure, such as a TLIF spinal procedure, in accordance with an embodiment of the invention. FIG. 2 also shows the arrangement of the implant 10b, driver 20 and flexible connector 30 (in phantom) after the implant 10b has been positioned in its final location where the implant may be expanded. As shown in FIG. 2, the implant 10a is initially grasped by the driver 20, which has a shaft 21 and a handle 22. The driver 20 includes a stationary arm 23 and a pivoting arm 25, as more fully described below. Although not shown in FIG. 2, an axially movable sleeve may be provided around the shaft 21 to force the pivoting arm 25 into the closed position (shown by the solid line) when the sleeve is extended away from the handle 22, and to allow the pivoting arm 25 to move to the open position (shown in phantom) when the sleeve is retracted toward the handle 22.

As further shown in FIG. 2, the flexible connector 30 releasably couples the driver 20 to the implant 10a, 10b. In the embodiment shown, the flexible connector 30 has a proximal end 31 connected to the driver 20 by means of a releasable engagement mechanism 27. The flexible connector 30 also has a distal end 32 connected to the implant 10a. As shown in phantom in FIG. 2, the implant may be moved to the position labeled as 10b while the pivoting arm 25 has been rotated away from engagement with the implant 10b, and the flexible connector 30 bends but remains connected to the driver 20 and insert 10b.

In certain embodiments, the flexible connector 30 comprises a helical spring having sufficient flexibility to bend laterally, but sufficient torsional stiffness to transfer torque from the driver 20 to the implant 10 during the expansion operation. For example, the flexible connector 30 may comprise a double helical spring or a double start spring with two elements, one wound clockwise and one wound counterclockwise. Such a counterwound double helical arrangement may add torsional stability to prevent buckling or permanent deformation when the spring is tensioned with high forces. Examples of flexible helical couplings that may be adapted for use in accordance with the present invention include commercially available helical springs sold under the designation Heli-Cal by Helical Products Company, Inc. The flexible connector 30 may have any suitable dimensions, for example, a length of from 3 to 50 mm, and an outer diameter of from 1 to 10 mm.

Figure 3:
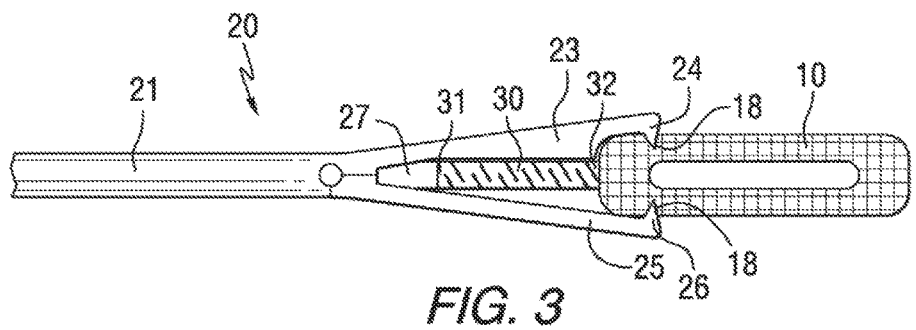
FIG. 3 is a partially schematic top view.
Figure 4:
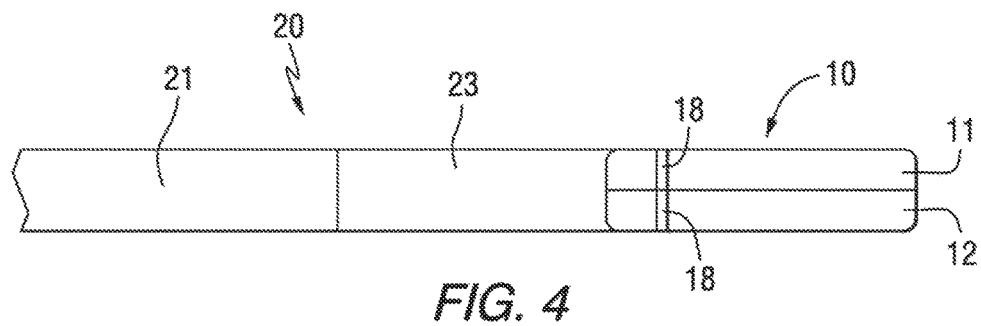
FIGS. 4 and 5 are partially schematic side views, illustrating engagement between a driver and an expandable implant in accordance with an embodiment of the present invention.
Figure 5:
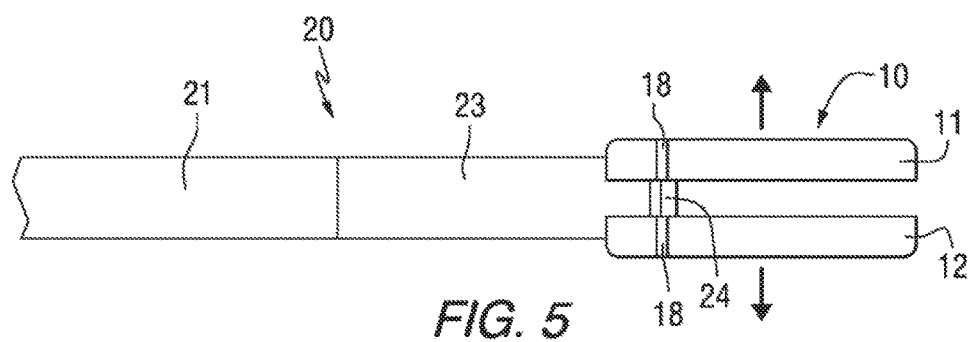

FIGS. 3-5 schematically illustrate an arrangement of an expandable implant 10 and a driver 20. As shown in the top view of FIG. 3, the shaft 21 of the driver 20 has a distal end including a stationary arm 23 and a pivoting arm 25. The stationary arm 23 includes a grip tooth 24 comprising an extended ridge having a generally V-shaped cross section. The pivoting arm 25 includes a similar grip tooth 26. As shown in FIG. 3, each of the grip teeth 24 and 26 engage a grip recess 18 in the implant 10, comprising a generally V-shaped groove running vertically from the top to bottom of the insert 10.

FIGS. 4 and 5 are side views schematically illustrating expansion of the implant 10. The implant 10 includes an upper plate 11 and a lower plate 12 that may be expanded away from each other from a contracted position as shown in FIG. 4 to an expanded position as shown in FIG. 5. For purposes of illustration, the pivoting arm 25 is not shown in FIG. 4 or 5. As most clearly shown in FIG. 5, as well as in FIG. 3, when the upper and lower plates 11 and 12 expand away from each other, the grip tooth 24 on the stationary arm 23 may remain engaged with the respective grooves 18 in the upper and lower plates 11 and 12. In this manner, the stationary arm 23 of the driver 20 may remain engaged with the implant 10 not only during placement of the implant 10 in the desired location within the spine, but also during subsequent expansion of the implant 10.

Figure 6:
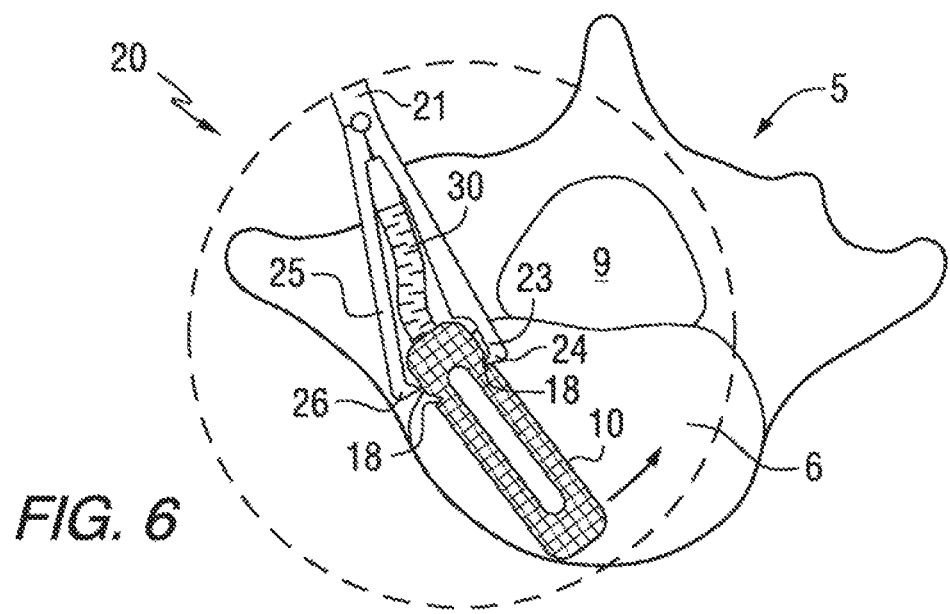
FIG. 6 is a partially schematic top view.
Figure 7:
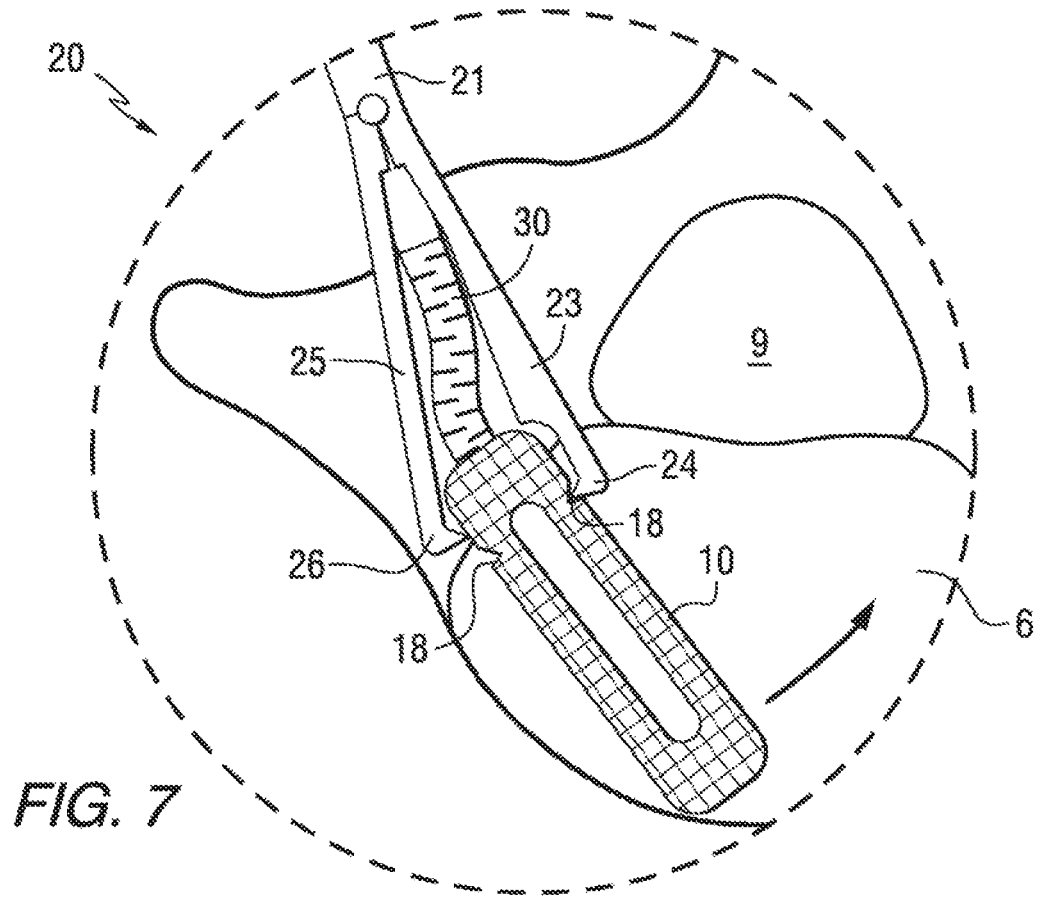
FIG. 7 is an enlarged portion of FIG. 6, illustrating an intermediate stage of a TLIF spinal procedure utilizing an expandable implant, driver and flexible connector in accordance with an embodiment of the present invention.

FIGS. 6 and 7 schematically illustrate an intermediate stage of a TLIF spinal procedure in which the implant 10 has been inserted into the region of the anterior one-third of the vertebral body 6, and is being rotated toward its final transverse position. The trajectory of the implant 10 starts approximately parallel to the direction of the two adjacent spinal pedicles on the ipsilateral side of the spine. As the spinal implant 10 is rotated it is turned by the implant driver 20 into a position such that the long axis of the implant is in the translateral or transverse axis. As shown most clearly in the enlarged view of FIG. 7, the stationary arm 23 and its grip tooth 24 may remain engaged in the respective grip recesses 18 of the implant. However, the pivoting arm 25 has been rotated to a position as shown in which its grip tooth 26 has disengaged from its corresponding grip recesses 18 in the insert 10. Although the grip tooth 26 of the pivoting arm 25 has been disengaged, contact may still be maintained between an inner surface of the pivoting arm 25 and an end corner of the implant 10. As further shown in FIG. 7, at this stage of the procedure, the flexible connector 30 bends but is still secured to both the driver 20 and implant 10. In certain embodiments, the flexible connector 30 may also expand or contract along its longitudinal axis, e.g., the connector 30 may comprise a helical spring that extends and/or compresses during stages of the procedure.

Figure 8:
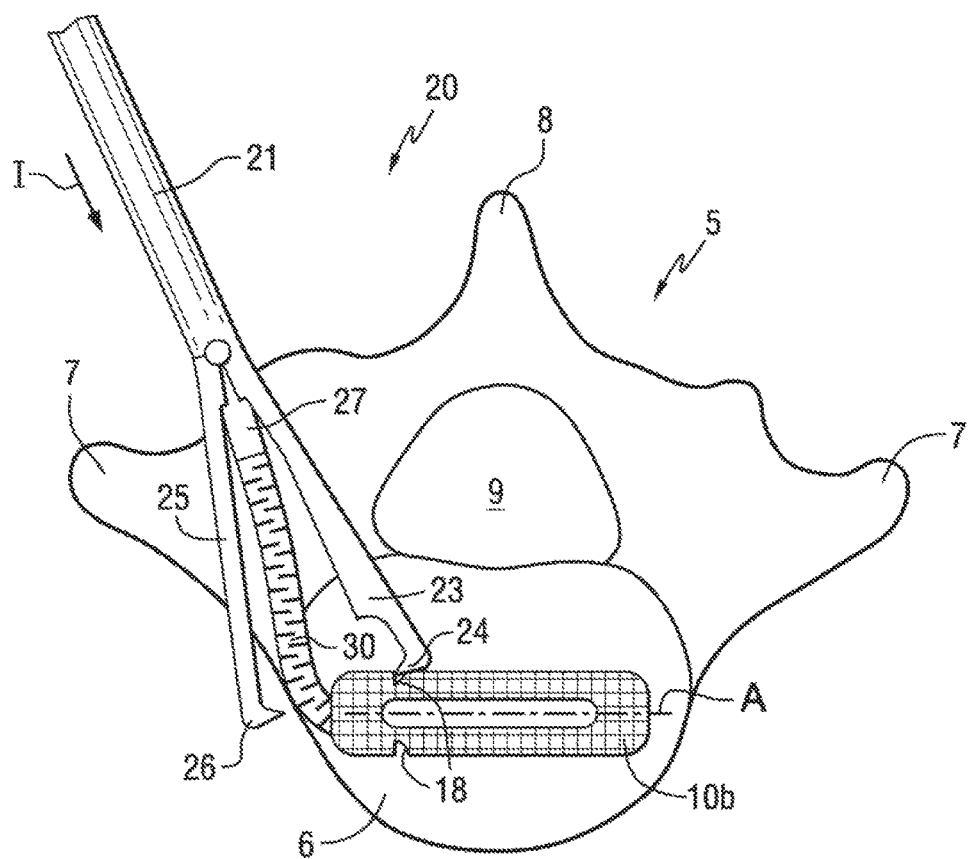
FIG. 8 is a partially schematic top view illustrating a TLIF spinal procedure in which an expandable implant has been placed in its final position and may be expanded using a driver and flexible connector in accordance with an embodiment of the present invention.

FIG. 8 illustrates a subsequent stage of a TLIF spinal procedure in which the implant 10b is located at its desired transverse position in relation to the anterior one-third of the vertebral body 6. The long axis of the implant 10b is in the transverse orientation, i.e., the line bisected by the anatomic transverse and coronal planes. In this position, the grip tooth 24 of the stationary arm 23 may still remain in contact with the corresponding grip recesses 18 of the implant 10b, however, the pivoting arm 25 may no longer contact the implant 10b. During the stages shown in FIGS. 6-8, the stationary arm 23 may be used in various ways to push or otherwise force the implant into position. For example, instead of maintaining contact between the grip tooth 24 and the grip recesses 18 during the entire procedure, the arm 23 may be manipulated by the surgeon in any desired manner to contact various parts of the implant 10 with various parts of the arm 23 to move the implant into the desired position.

After the implant 10b has been moved into position as shown in FIG. 8, torque may be applied to the driver 20 to rotate the flexible connector 30 in order to expand the implant 10b, as more fully described below. After the expansion step is completed, the driver 20 is disengaged from the implant 10b. In one embodiment, the driver 20 is disengaged by releasing the flexible connector 30 from the driver 20. In another embodiment, the driver 20 is disengaged by disengaging the flexible connector 30 from the implant 10b.

FIGS. 9-12 schematically illustrate embodiments of expandable implants 10 in accordance with the present invention. In the embodiment shown in FIG. 9, the implant 10 includes upper and lower plates 11 and 12 comprising angled expansion ramps 13 on their inwardly facing surfaces. A threaded expansion rod 14 extends along the longitudinal axis of the implant 10 in the region between the upper and lower plates 11 and 12. Internally threaded expansion wedges 15 are threaded onto the expansion rod 14. The threaded expansion rod 14 may be rotated around its longitudinal axis by turning the flexible connector 30. Rotation of the flexible connector 30, and the resultant rotation of the threaded expansion rod 14, causes the internally threaded expansion wedges 15 to move axially along the rod 14 with their upper and lower exterior surfaces sliding along the expansion ramps 13. When the wedges 15 move toward each other, the upper and lower plates 11 and 12 expand away from each other. While the expansion wedges 15 may be have cross-sectional shapes that are circular or otherwise rounded, in a preferred embodiment, the expansion wedges 15 have square or rectangular cross sections that prevent the wedges from rotating around their central longitudinal axes. In this embodiment, the expansion ramps 13 may comprise substantially flat surfaces contacting correspondingly flat surfaces of the expansion wedges 15.

In the embodiment shown in FIG. 10, the upper and lower plates 11 and 12 of the implant 10 have a similar configuration as shown in the embodiment of FIG. 9. However, the implant 10 has generally conical expansion wedges 17 that are externally threaded, and an expansion rod 16 is not threaded. In this embodiment, the expansion ramps 13 are preferably concave with conical surfaces that contact the threads of the conical externally threaded wedges 17. In this embodiment, the cross-sectional shape of the expansion rod 16 may be non-circular, and the externally threaded wedges 17 may have correspondingly shaped holes extending axially therethrough with sufficient clearance for the wedges 17 to axially slide along the expansion rod 16. In this manner, the externally threaded wedges 17 may be free to slide along the axial length of the expansion rod 16, but are constrained to rotate with the expansion rod 16 when the expansion rod 16 is rotated around its longitudinal axis. Rotation of the flexible connector 30 causes the expansion rod 16 and externally threaded wedges 17 to rotate around their longitudinal axes, while the wedges 17 are free to slide along the axial length of the expansion rod 16. Contact between the external threads of the wedges 17 and the conically shaped inner surfaces of the expansion ramps 13 causes the wedges 17 to move axially toward each other, which results in expansion of the upper and lower plates 11 and 12 away from each other.

Figure 11:
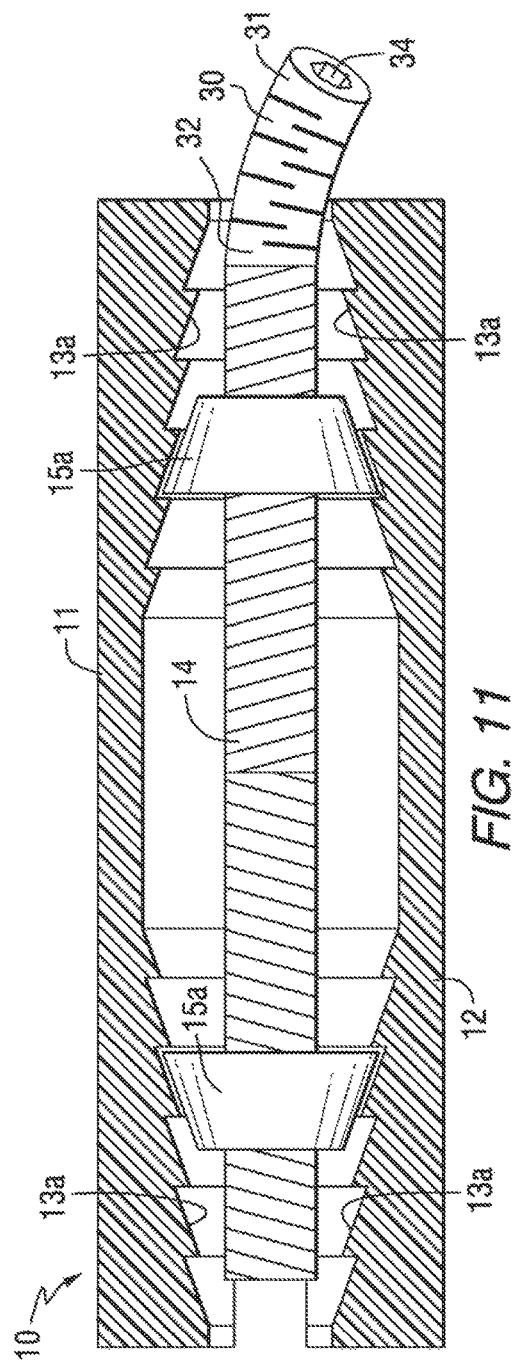
FIG. 11 is a partially schematic side view of an expandable implant and flexible connector in accordance with a further embodiment of the invention.

The embodiment shown in FIG. 11 is similar to the embodiment shown in FIG. 9, except the expansion ramps 13a of the upper and lower plates 11 and 12 are oriented in opposite directions, and the wedges 15a are likewise oriented differently. In this embodiment, rotation of the flexible connector 30 causes the wedges 15a to move away from each other along the longitudinal axis of the threaded expansion rod 14. As the wedges 15a move away from each other, their exterior surfaces slide against the interior surfaces of the expansion ramps 13a, thereby forcing the upper and lower plates 11 and 12 away from each other.

As shown in FIGS. 9-11, the distal end 32 of the flexible connector 30 is attached to one end of the expansion rod 14 or 16. It is noted that in the embodiments shown in FIGS. 9-11, the flexible connector 30 is illustrated as bending in a downward direction, however, it is to be understood that the flexible connector 30 may also bend in other directions, for example, into the page and/or out of the page in FIGS. 9-11. In the embodiments shown, the distal end 32 of the flexible connector 30 includes a hexagonal recess 34 configured to receive the head of a releasable engagement mechanism 27 of the driver 20, as more fully described below. In the embodiment shown, the distal end 32 of the flexible connector 30 may be permanently secured to the end of the expansion rod 14 or 16, while the proximal end 31 of the flexible connector 30 may be releasably engaged with the driver 20. Alternatively, the distal end 32 may be releasably engaged with the expansion rod 14 or 16, while the proximal end 31 may remain engaged with the driver 20. For example, the distal end 32 of the flexible connector 30 may have a hex-head projection or recess that matingly engages a corresponding hex-head recess or projection at the end of the expansion rod 14 or 16. Such a hex-head connection may be sufficiently tight such that the connection is maintained during the steps of inserting, positioning, and expanding the implant, but may be disengaged after the implant is expanded by pulling the driver back with sufficient force remove the hex-head projection from the recess.

Figure 12:
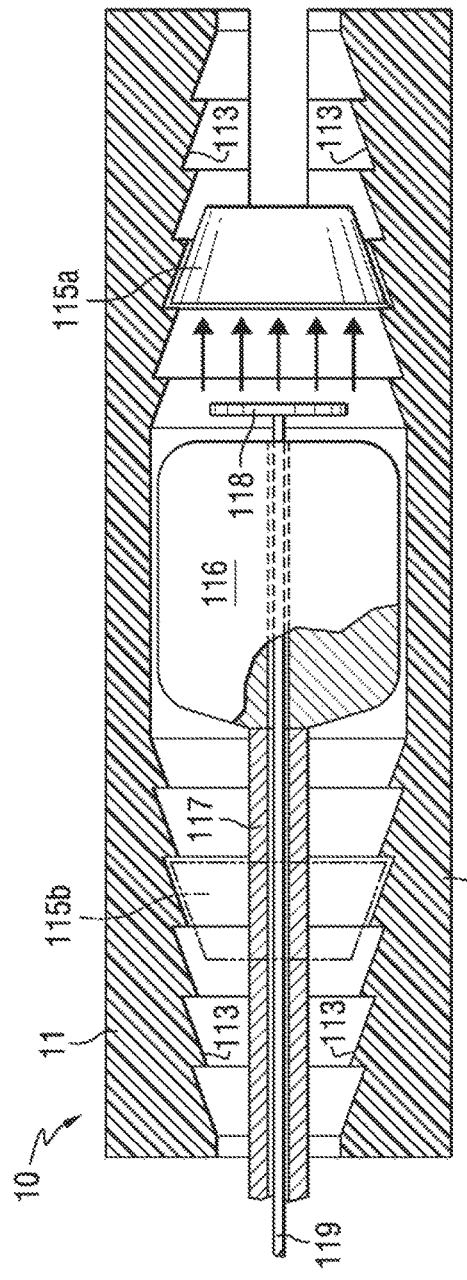
FIG. 12 is a partially schematic side view of an expandable implant and flexible connector in accordance with another embodiment of the invention.

FIG. 12 schematically illustrates another embodiment of an expandable implant 10 in which the upper and lower plates 11 and 12 are expanded away from each other by means of a distractor paddle 116 having an outer cam surface that contacts inner surfaces of the upper and lower plates 11 and 12 and forces them away from each other when the paddle 116 is rotated around its longitudinal axis. The upper and lower plates 11 and 12 include expansion ramps 113 having surfaces that engage expansion wedges 15a and 15b. During the expansion procedure, the distractor paddle 116 is rotated to spread the upper and lower plates 11 and 12 away from each other, then a pusher 118 is used to move the first expansion wedge 115a into a desired axial location where contact between the outer surface of the expansion wedge 115a and the expansion ramps 113 results in the desired amount of expansion of the upper and lower plates 11 and 12. Next, the distractor paddle 116 may be rotated by the paddle shaft 117 to a position in which there is sufficient clearance between the distractor paddle 116 and the inner surfaces of the upper and lower plates 11 and 12 to allow the distractor paddle 116 to be at least partially removed from the region between the upper and lower plates 11 and 12. The paddle shaft 117 is thus used to rotate and axially move the distractor paddle 116. Upon removal of the distractor paddle 116, the interior space between the upper and lower plates 11 and 12 may be packed with bone material or the like in order to facilitate fusion of the implant 10 into the spinal structure. After the interior space is packed with material, the second expansion wedge 115b may be moved into a desired axial position by inserting it through the proximal end of the implant 10. The wedge 115b may be placed with a screwdriver or other tool (not shown) which rotates the wedge 115b 90 degrees after it is inserted deep into the proximal end of the central cavity of the implant 10. The proximal wedge 115b may have an oblong or elliptical cross-sectional shape. The proximal wedge 115b may be inserted past the proximal ramp steps or teeth, and then rotated 90 degrees such that its largest dimension of the ellipse is from cephalad to caudad. The proximal wedge 115b may then be pulled toward the ipsilateral open end of the implant until the smallest ramp is engaged or tight. The proximal wedge 115b may thus be pulled away from the other wedge 115a, and then rotated around its longitudinal axis to contact the expansion ramps 113 of the upper and lower plates 11 and 12. The expansion wedges 115a and 115b may have non-circular cross sections which facilitate placement of the wedges in their desired axial locations, and retention in those positions in contact with the expansion ramps 113.

The dimensions used for the various components of the expandable implants 10 may be selected as desired. For example, a typical implant 10 may expand 10 percent to 100 percent of its original compact height, e.g., an implant may have a compact height of 8 mm and an expanded height of 12 mm. Any suitable length of implant may be used, for example, from 10 to 80 mm, e.g., 50 mm.

In the embodiments shown in FIGS. 9-12, the expansion ramps 13, 13a and 113 may be sized and arranged as desired. For example, each expansion ramp 13, 13a, 113 may have a dimension of 1 mm high and 1 mm in width, with a 10 to 15 degree ramp angle. In certain embodiments, the ramps may be used to incrementally raise the height of an implant, e.g., from 8 mm to 9 mm to 10 mm to 11 mm to 12 mm in succession. The upper and lower plates 11 and 12 of the implants 10 may have openings of suitable sizes that allow bony ingrowth through the fusion cage, e.g., approximately 5 mm by 20 mm in size.

The wedges, rods and other components of the expansion mechanisms may be made of any suitable material such as titanium, while the upper and lower prosthetic endplates 11 and 12 may be made of poly-ether-ether-ketone (PEEK) or other suitable materials. The components of the driver 20 and flexible coupling 30 may be made of suitable materials such as stainless steel, titanium, and the like.

In certain embodiments, the expandable implants may be manufactured of known radiolucent material to allow radiographic visualization of the bone graft healing and incorporation. The flexible driver allows the surgeon to reference the radiolucent implant orientation via a more constrained and predictable junction. A more secure linkage makes it easier to exchange preparation instruments, soft tissue protective cannulas, trochars, particularly while inserting implants over guidewires.

Figure 13:
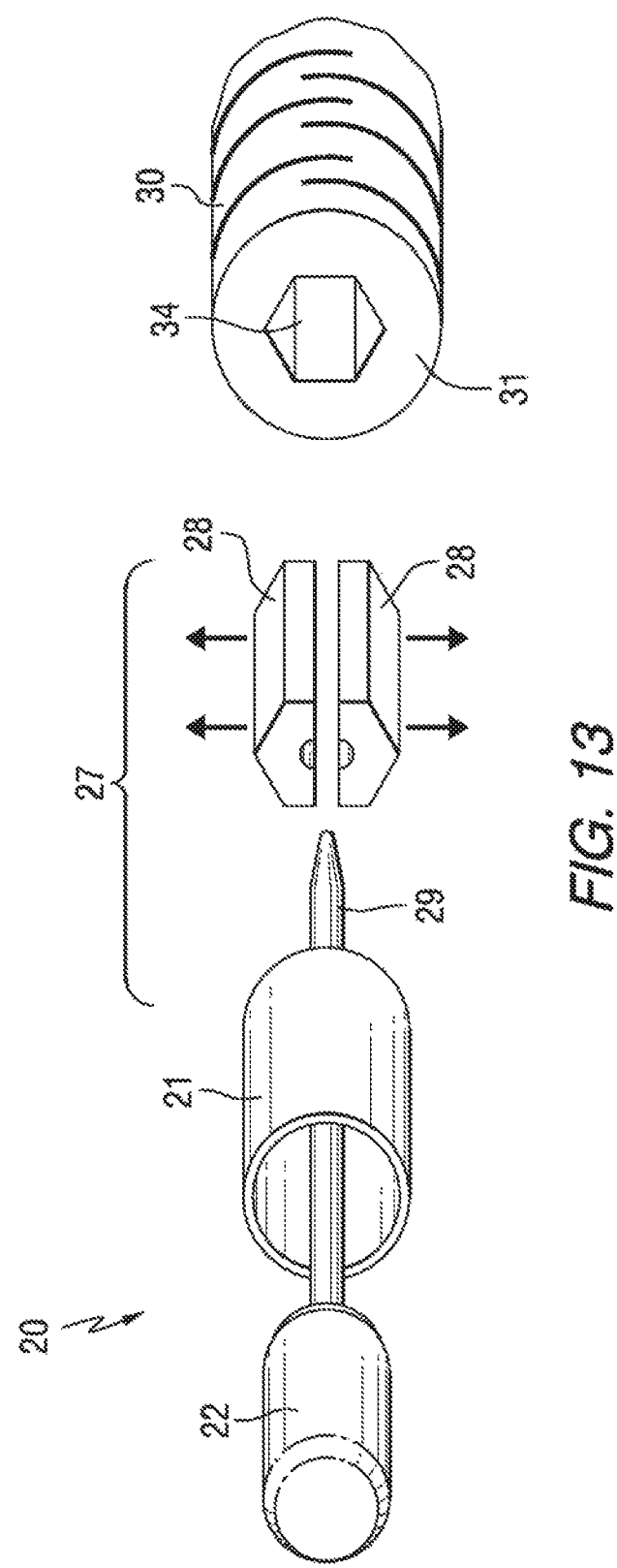
FIG. 13 is a partially schematic exploded end perspective view showing a release mechanism for disengaging a driver from a flexible connector in accordance with an embodiment of the invention.

FIG. 13 schematically illustrates a release mechanism 27 for engaging and disengaging the driver 20 from the flexible connector 30. It is noted that the various components are not drawn to scale in FIG. 13, but are provided for illustration purposes. In the embodiment shown, the release mechanism 27 comprises a hex-head connector including radially movable engagement members or jaws 28. The outer surfaces of the jaws 28 are configured to engage respective inner surfaces of the hex head recess 34 of the flexible connector 30. When the jaws 28 are inserted into the recess 34 and forced radially away from each other, they engage and are secured in the recess 34. An axially movable rod plunger 29 is used to force the jaws 28 radially away from each other by insertion of its tapered head into opposing semi-circular channels in the interior surfaces of the jaws 28. The rod plunger 29 is axially movable inside the cannulated driver shaft 21. Although not shown in FIG. 13, the jaws 28 may be biased radially towards each other, for example, through the use of tension springs (not shown). Thus, when the rod plunger 29 is retracted along its longitudinal axis away from the jaws 28, the jaws 28 collapse toward each other, thereby disengaging their outer surfaces from the recess 34 of the flexible connector 30.

Although not shown in FIG. 13, the rod plunger 29 can also be threaded to create a smoother insertion without a need for hammering or impaction force. Although a hex-head connection using two radially movable jaws is shown in FIG. 13, it is to be understood that any other suitable type of releasable coupling may be used in accordance with the present invention. For example, instead of two jaws 28 as shown in FIG. 13, three, four, five, six, or more radially expandable jaws or pivot arms may be used. Furthermore, although a hexagonal recess 34 is shown in FIG. 13, any other suitable recess configuration could be used, such as square, rectangular, triangular, oval and the like. Although the driver 20 is releasably attached to the flexible connector 30 in the embodiment shown in FIG. 13, the flexible connector 30 may alternatively be releasably attached to the implant, e.g., by a coupling similar to that shown in FIG. 13 with a flexible rod plunger extending through a cannulated central opening through the flexible connector 30, a tight-fitting hex head connection that can be disengaged after the implant is expanded by pulling the driver and flexible connector away from the expanded implant with sufficient force, or the like.

The instruments of the present invention allow an implant to be optimally positioned before it is expanded. For example, a TLIF implant can be placed at an angle of up to 90 degrees from the posterior angle of insertion. Such a procedure allows a minimally invasive approach, as the incision and exposure do not have to be extended to allow manipulating or turning the expandable implant. This allows moving a TLIF implant into the preferred direct transverse orientation before opening.

In certain embodiments, the invention allows for expansion of an expandable XLIF implant with minimally invasive exposure. Often with a deformity, or with multiple procedures performed through the same small incision, the orientation of the interbody fusion changes as the deformity is reduced. The angle of performance of the XLIF and the disk space changes by the end of the case. This is common especially when dealing with L4-L5 and especially when dealing with the reduction of a scoliotic deformity. The flexible driver of the present invention allows for fine tuning, readjustment, backing off, re-expansion and balancing the expansion between the multiple XLIF implants at the end of the procedure.

The flexible driver of the present invention may be used in other types of minimally invasive spine surgery. In such MIS procedures, the approach is through a tube, narrow corridor, or confined space. This puts a premium on screwing, drilling, tapping, cutting screw threads, and performance of other maneuvers through a confined corridor without the ability to alter the angle of trajectory of the tool shaft. The flexible driver of the present invention helps solve this mechanical challenge by applying a rotational force at an angle from the insertion direction.

In certain embodiments, anchorage of a stand alone anterior lumbar interbody fusion (STALIF) type cages or interbody spacers is facilitated by an angled driver with a helical spring flexible component. This is particularly useful as the implant surgery becomes more minimally invasive.

In certain types of procedures, two expandable implants may be positioned side by side in the intervertebral disk space. If the expandable implant that is anterior is expanded and the posterior expandable implant is collapsed then this would increase and adjust the amount of spinal lordosis. On the contrary, if the reverse occurs with the anterior implant collapsing and the posterior implant expanding then this would increase the amount of kyphosis.

In certain other types of procedures, two expandable implants may be placed laterally end-to-end and individually adjusted. The expandable implants could adjust the amount of coronal balance, and scoliosis correction could be adjusted after implant insertion at multiple levels but before closing the skin. By adjusting and expanding the implants differentially, the spine can tilt left or right. Thus, the functional spinal unit can be used to correct scoliosis apex toward the left or the right. The functional spinal units with expandable implants may be stacked one above another such as from T12 to L3 in order to correct a thoracolumbar scoliosis.

Whereas particular embodiments of this invention have been described above for purposes of illustration, it will be evident to those skilled in the art that numerous variations of the details of the present invention may be made without departing from the invention as defined in the appended claims.

What is claimed is:

1. A surgical system comprising:
    a driver;
    an expandable spinal implant comprising upper and lower plates configured to expand away from each other in a first axis, wherein the expandable spinal implant includes an expansion mechanism comprising a rotatable expansion rod positioned on a second axis perpendicular to the first axis and at least one wedge axially movable on the expansion rod, and at least one of the upper and lower plates comprises at least one ramp surface in contact with the at least one wedge, and wherein rotation of the expansion rod causes the at least one wedge to move axially along the expansion rod and to engage the ramp surface to thereby expand the upper and lower plates away from each other; and
    a flexible connector extending outside of the expandable spinal implant, the flexible connector connected to the driver at a first end and the expansion rod at a second end, wherein the flexible connector is rotatable by the driver to expand the spinal implant,
    wherein the at least one wedge includes a ramp surface that contacts the at least one ramp surface of at least one of the upper and lower plates when the expansion rod is rotated,
    wherein the second axis extends in a manner that is substantially straight from a proximal end of the implant to a distal end of the implant, wherein the proximal end of the implant is configured to connect to the flexible connector and the distal end of the implant is configured to be an insertion point of the implant between adjacent vertebral bodies.

2. The surgical system of claim 1, wherein the flexible connector comprises a helical spring.

3. The surgical system of claim 2, wherein the helical spring comprises a counterwound double helical spring.

4. The surgical system of claim 1, wherein the flexible connector is releasably attached to the driver.

5. The surgical system of claim 4, wherein the flexible connector is permanently attached to the implant.

6. The surgical system of claim 1, wherein the flexible connector is releasably attached to the implant.

7. The surgical system of claim 1, wherein the driver further comprises at least one grip arm releasably engageable with the implant.

8. The surgical system of claim 1, wherein the driver further comprises at least two grip arms releasably engageable with the implant, and at least one of the grip arms is pivotable into engagement with the implant.

9. The surgical system of claim 8, wherein the flexible connector is positioned between the at least two grip arms of the driver.

10. The surgical system of claim 1, wherein the upper plate has a side surface having a first groove and the lower plate has a side surface having a second groove adjacent to the first groove, and the first and second grooves are configured to be engaged by a grip tooth on the driver.

11. The surgical system of claim 1, wherein the expansion rod is rotated around its longitudinal axis by turning the flexible connector.

12. The surgical system of claim 1, wherein the at least one wedge is internally threaded and is threaded onto external threads on the expansion rod.

13. A surgical instrument comprising:
    a driver having a proximal end and a distal end;
    a spinal implant; and
    a flexible connector releasably attached to the distal end of the driver, wherein the flexible connector is structured and arranged to engage and expand the spinal implant when torque is applied to the flexible connector from the driver, wherein a distal end of the flexible connector is attached to one end of a rotatable expansion rod, a proximal end of the flexible connector extends outside of the spinal implant, and the spinal implant is expanded when rotation of the expansion rod causes at least one wedge to move axially along the expansion rod to thereby expand the spinal implant
    wherein the spinal implant includes an upper plate and a lower plate configured to expand in a first axis,
    wherein the expansion rod is positioned within the spinal implant along a second axis that is perpendicular to the first axis,
    wherein the at least one wedge includes a ramp surface that contacts at least one ramp surface of the upper plate when the expansion rod is rotated,
    wherein the second axis extends in a manner that is substantially straight from a proximal end of the implant to a distal end of the implant, wherein the proximal end of the implant is configured to connect to the flexible connector and the distal end of the implant is configured to be an insertion point of the implant between adjacent vertebral bodies.

14. The surgical instrument of claim 13, wherein the distal end of the driver comprises a hex-head connector including at least two radially expandable engagement members releasably engageable with the flexible connector.

15. A method of positioning and using a surgical instrument in a patient comprising:
grasping an implant with a driver in an aligned insertion orientation, the driver having a proximal end and a distal end;
a flexible connector releasably attached to the distal end of the driver, wherein the flexible connector is structured and arranged to engage and expand a spinal implant comprising upper and lower plates expandable away from each other in a first axis, the flexible connector extending outside of the spinal implant;
positioning the implant in the patient at a desired position while rotating the implant from the aligned insertion orientation to an angled orientation;
expanding the implant with the driver while the implant is in the angled orientation, wherein the spinal implant includes an expansion mechanism comprising a rotatable expansion rod and at least one wedge axially movable on the expansion rod, and at least one of the upper and lower plates comprises at least one ramp surface in contact with the at least one wedge, and wherein rotation of the expansion rod causes the at least one wedge to move axially along the expansion rod and to engage the ramp surface to thereby expand the upper and lower plates away from each other; and
disengaging the driver from the implant,
wherein the expansion rod is positioned within the spinal implant along a second axis that is perpendicular to the first axis,
wherein the second axis extends in a manner that is substantially straight from a proximal end of the implant to a distal end of the implant, wherein the proximal end of the implant is configured to connect to the flexible connector and the distal end of the implant is configured to be an insertion point of the implant between adjacent vertebral bodies.

16. The method of claim 15, wherein the driver and implant are releasably connected to each other by the flexible connector.

17. The method of claim 16, wherein the implant is expanded by rotating the driver to thereby apply torque through the flexible connector to the expansion mechanism in the implant.

* * * * *